(12) United States Patent
Gan et al.

(10) Patent No.: US 11,167,002 B2
(45) Date of Patent: Nov. 9, 2021

(54) PHARMACEUTICAL COMPOSITION FOR THE TREATMENT OF MALIGNANT NEOPLASMS INCLUDING SARCOMA, CANCERS OF LIVER, LUNG, BLADDER, BLOOD AND CERVICAL, TREATMENT OF INFECTIOUS DISEASES AND TYPE 2 DIABETES

(71) Applicant: David Xiage Gan, Rockville, MD (US)

(72) Inventors: David Xiage Gan, Rockville, MD (US); Zheng Cui, Kernersville, NC (US)

(*) Notice: Subject to any disclaimer, the term of this patent is extended or adjusted under 35 U.S.C. 154(b) by 0 days.

(21) Appl. No.: 16/577,605

(22) Filed: Sep. 20, 2019

(65) Prior Publication Data
US 2021/0077561 A1    Mar. 18, 2021

Related U.S. Application Data

(60) Provisional application No. 62/891,947, filed on Aug. 26, 2019.

(51) Int. Cl.
*A61K 36/8962*    (2006.01)

(52) U.S. Cl.
CPC .... *A61K 36/8962* (2013.01); *A61K 2236/333* (2013.01); *A61K 2236/53* (2013.01)

(58) Field of Classification Search
CPC .......... A61K 2236/333; A61K 2236/53; A61K 36/8962; A61K 47/26; A61K 9/0019; A61P 31/04; A61P 31/10; A61P 31/12; A61P 35/00; A61P 35/02; A61P 3/10
See application file for complete search history.

(56) References Cited

FOREIGN PATENT DOCUMENTS

CN    100506962 C   *   7/2009

OTHER PUBLICATIONS

Li Z; Le W; Ciu Z "A novel therapeutic anticancer property of raw garlic extract via injection but not ingestion" Cell Death Discovery (2018) 4(1):108, p. 1-10; doi10.1038/s41420-018-0122-x (Year: 2018).*

* cited by examiner

*Primary Examiner* — Aaron J Kosar

(57) ABSTRACT

The present invention relates to a pharmaceutical composition. The pharmaceutical composition is the organic phase of raw garlic (*Allium sativum*, all species) or water extraction to provide novel cancer treatments of multiple malignant neoplasms, infectious diseases and Type 2 diabetes. The effective formulation of OPRGE is either liquid or dry powder of OPRGE; the effective routes of administration is intravenous (IV) for infectious diseases and diabetes; the effective routes of administration is intravenous (IV) or intraperitoneal (IP) or intratumoral infusions for malignant neoplasms. The patent application consistent of OPRGE extraction methods, mode of administration of OPRGE and clinical indications.

5 Claims, No Drawings

PHARMACEUTICAL COMPOSITION FOR THE TREATMENT OF MALIGNANT NEOPLASMS INCLUDING SARCOMA, CANCERS OF LIVER, LUNG, BLADDER, BLOOD AND CERVICAL, TREATMENT OF INFECTIOUS DISEASES AND TYPE 2 DIABETES

CROSS REFERENCE TO RELATED APPLICATIONS (IF ANY)

(Related applications may be listed on an application data sheet, either instead of or together with being listed in the specification.)
No related applications.

STATEMENT OF FEDERALLY SPONSORED RESEARCH OR DEVELOPMENT (IF ANY)

No Federally Sponsored Research or development
The names of the parties to a joint research agreement if the claimed invention was made as a result of activities within the scope of a joint research agreement
No joint research agreement.

BACKGROUND OF THE INVENTION

Field of Invention

The present invention relates generally to a pharmaceutical composition, its routes of administration, and its use. More specifically, the present invention is a pharmaceutical composition of garlic extractions, the organic phase of raw garlic extraction (OPRGE) and the water extraction of raw garlic (WERG) to treat malignant tumors by IV, IP or intratumor administrating, treating Type 2 diabetes, and treating infectious diseases caused by microorganisms.

Prior to this submission, intravenous, intraperitoneal and intratumor infusion of garlic or its extraction of the organic phase of raw garlic extraction (OPRGE) and the water extraction of raw garlic (WERG) have not been reported for the treatments of cancer, diabetes and infectious diseases or for any other indications.

Background of Invention

Despite great efforts in developing new products to treat cancers, infectious diseases, and diabetes, there are still great medical needs for treating/managing these conditions.

The World Health Organization (WHO) note that, worldwide, nearly 1 in 6 deaths are down to cancer. In the United States alone, the National Cancer Institute (NCI) estimated 1,688,780 new cancer cases and 600,920 cancer-related deaths in 2017. Currently, the most common types of cancer treatment are chemotherapy, radiotherapy, tumor surgery, and—in the case prostate cancer and breast cancer—hormonal therapy. Innovations in cancer treatment aim to address a set of issues that will typically face healthcare providers and patients, including aggressive treatment accompanied by unwanted side effects, tumor recurrence after treatment, surgery, or both, and aggressive cancers that are resilient to widely utilized treatments. Innovations in cancer treatment aim to address a set of issues that will typically tare healthcare providers and patients, including aggressive treatment accompanied by unwanted side effects, tumor recurrence after treatment, surgery, or both, and aggressive cancers that are resilient to widely utilized treatments.

In 1990, the US National Cancer Institute concluded garlic may be a food with cancer-preventive properties. However, after extensive research efforts, there is no convincing evidence in animals or humans to support its therapeutic effect for malignant tumors via oral ingestion.

It is therefore an aim of the present invention to provide an alternative composition via. IV, IP administration route for treating cancers.

To treat bacterial infections, a variety of antibiotics drugs are available. However, the over-prescription of antibiotics over the past half century give rise to antibiotic resistant strains of bacteria such as superbugs. Antibiotic resistance microorganisms are increasing at an alarming rate. A growing list of infections i.e., pneumonia, tuberculosis, and gonorrhea are becoming harder and at times impossible to treat while antibiotics are becoming less effective. Antibiotic-resistant infections correlate with the level of antibiotic consumption. Non-judicial use of antibiotics is mostly responsible for making the microbes resistant. The antibiotic treatment repertoire for existing or emerging hard-to-treat multidrug-resistant bacterial infections is limited, resulting in high morbidity and mortality report. ncbi.nlm.nih.gov/pmc/articles/PMC5573035/.

For viral infections in general, and upper respiratory viral infections, effective drugs to hinder reproduction of the infectious agents are much less available. Prescription of anti-flu drugs currently available may reduce complications such as pneumonia, and often viruses are resistant to drugs.

As an alternative to conventional pharmaceuticals for treating bacterial or viral infection, interest has grown in the use of certain food supplements for the enhancing or stimulating the immune system in the human body. However, after extensive research efforts, there is no convincing evidence in animals or humans to support its therapeutic effect for infectious diseases caused by microorganisms via oral administration of garlic products.

To treat bacterial infections a variety of antibiotics drugs are available. However, the over-prescription of antibiotics over the past half century give rise to antibiotic resistant strains of bacteria such as superbugs.

It is therefore an aim of the present invention to provide an alternative composition via IV administration route for treating infectious diseases.

According to the analysis results of global data, the prevalence of diabetes mellitus in adults was about 153 million in 1980 and 347 million in 2008 [1]. It is estimated to increase to 439 million in 2030, with a 69% increase in developing countries and 20% in developed countries [2]. Type 2 diabetes mellitus (T2DM) is a global pandemic, chronic, progressive, incompletely understood metabolic condition chiefly characterized by hyperglycemia. Impaired insulin secretion, resistance to tissue actions of insulin, or a combination of both are thought to be the commonest reasons contributing to the pathophysiology of T2DM, a spectrum of disease originally arising from tissue insulin resistance and gradually progressing to a state characterized by complete loss of secretory activity of the beta cells of the pancreas. ncbi.nlm.nih.gov/pmc/articles/PMC5256065/. The ADA has released a range of recommendations called Standards of Medical Care in Diabetes to improve diabetes outcomes. The recommendations include cost-effective screening, diagnostic and therapeutic strategies to prevent, delay, or effectively manage T2DM and its life-threatening complications.

The terms of cancer and malignant neoplasms or malignant tumors are the defined the same.

Intravenous, intraperitoneal and intratumor infusion of garlic or its extraction of the organic phase of raw garlic extraction (OPRGE) and the water extraction of raw garlic (WERG) have not been reported for cancer treatments or for any other indications.

It is therefore an aim of the present invention to provide and alternative composition and IV, IP administration route for treating cancers; infections and diabetes.

BRIEF SUMMARY OF THE INVENTION

The present invention relates to a pharmaceutical. The pharmaceutical composition is the organic phase of raw garlic sativum, all species) OPRGE extraction of raw garlic to provide novel cancer treatments of multiple malignant neoplasms. The effective formulations of OPRGE are an intravenous (IV) formulation, intraperitoneal (IP) and intratumor1. The OPRGE IV, IP and intratumor formulations can be made from liquid OPRGE or OPRGE dry powder. OPRGE is extracted from water extraction of raw garlic (WERG). WERG can be administrated via IP or intratumor to provide novel cancer treatments of multiple malignant tumors. The present patent application consistent of ORGE extraction methods, mode of administration of OPRGE and clinical indications.

DETAILED DESCRIPTION OF THE INVENTION

Throughout history, many different cultures have recognized the potential use of garlic for prevention and treatment of different diseases. Recent studies support the effects of garlic and its extracts in a wide range of applications. These studies raised the possibility of revival of garlic therapeutic values in different diseases. Different compounds in garlic are thought to reduce the risk for cardiovascular diseases, have anti-tumor and anti-microbial effects, and show benefit on high blood glucose concentration. ncbi.nlm.nih.gov/pmc/articles/PMC4103721/.

There are different garlic extracts are marketed globally as healthy foods or supplements, such as garlic oils, aged garlic extracts. All these garlic products are given by oral either as food or as medicinal products. None of these products are given via Intravenous routes.

The garlic extract in the present invention is the extraction of the organic phase of raw garlic extraction and can be administered intravenously.

The present invention is the description how water extraction of raw garlic (WERG) and organic phase of raw garlic extraction (OPRGE) are made.

Methods to make water extraction of raw garlic (WERG):

The sterilized raw garlic cloves are mixed with sterile water (H2O) at certain ratios, and high speed blended.

The blended garlic juice is filtered to remove particles to derive the water extraction of raw garlic (WERG) clear extracted solution.

Methods to make organic phase of raw garlic extraction (OPRGE):

The OPRGE is extracted from WERG based on solvent solubility.

For the separation based on hydrophobicity, an equal volume of chloroform/methanol (1:1) was added to WERG. After thorough homogenization, an equal volume of 1-butanol/50 mM NaCl (4:5, v/v) mixture was added before vortexing and sonicating till being completely mixed. The tubes were centrifuged in no less than 10 min at temperature of 45 F to 75 F. After centrifugation, the WERG is separated into 3 phases: a colorless upper aqueous phase; a white solid interphase; and a light yellowish lower organic phase. The aqueous phase and organic phase were collected carefully. The organic phase is dried with nitrogen gas to remove the methanol. The organic phase of raw garlic extraction (OPRGE) is completely dried under a flow of dry nitrogen. The dried OPRGE can be stored at −20° C. or −80° C. sealed with nitrogen gas for up to 12 months.

Methods to make organic phase of raw garlic extraction (OPRGE) IV infusion solution.

For intravenous infusion, the dried OPRGE is dissolved in 99.9% DMSO (dimethyl sulfoxide). The dissolved solution can be added the following the intravenous solutions based on medical needs up to 5% of DMSO and 5% of OPRGE.

- 0.9% Normal Saline (also known as NS, 0.9NaCl, or NSS)
- Lactated Ringers (also known as LR, Ringers Lactate, or RL)
- 5% Dextrose in Water (also known as D5 or D5W)
- 0.45% Normal Saline (also known as Half Normal Saline, 0.45NaCl)

Garlic has been used either as a medicinal food or a topical agent to treat many different medical conditions.

Effects of OPRGE on Cancers

In vivo: ascites malignancies induced by ip injections of sarcoma 180 (S180) cells or EL4 cells in mice of any strain represent the most aggressive model of malignancy in animals and probably humans. From the time of injection, the survival times of the mice are only 2-3 weeks unless they can be cured by the most effective therapy before death. Thus far, there has not been any therapy capable of treating these two types of malignant ascites in mice but with one exception.

In animal studies, oral administration of garlic extracts failed to cure animal malignant neoplasms. While peritoneal administration of fresh water garlic extract (WERG) and organic phase of raw garlic extraction (OPRGE) can cure animals with malignant neoplasms. Animals in control group with similar malignant neoplasms did not survive. The mechanism for the therapeutic effect is that the nutrients of raw garlic extracts could be utilized by normal cells but could be stalled as toxins in the cancer cells which are universally defective in many metabolic pathways. nature.com/articles/s41420-018-0122-x The lack of adverse side effect of OPRGE in mice. OPRGE showed specifically killing of cancer cells but not normal cells. This selective killing of cancer cells was also reflected in the treated mice that had neither visible physical side-effect nor abnormality in any organ or tissue upon necropsy.

Invitro. In studies both in vitro and on animals, it was shown that organic combinations of sulfur contained in garlic can suppress the incidence of many cancers, such as breast, blood, bladder, gastric, oral cavity, colorectal, skin, uterus, esophagus, and lung cancers. ncbi.nlm.nih.gov/pubmed/24964572

The cytotoxic effect of OPRGE against human malignant neoplasm cell lines. Cell cultures of cell lines of human bladder carcinoma, cervical cancer, chronic myelocytic leukemia, for 24 hours at 37° C. These cells were co-cultured with different extractions of OPRGE as indicated in the above figure for 24 hours at 37° C. Cancer cells died in the cell cultures with OPRGE. nature.com/articles/s41420-018-0122-x In 1990, the US National Cancer institute concluded garlic may be a food with cancer-preventive properties. However, after extensive research efforts, there is no convincing evidence in animals or humans to support its therapeutic effect for malignant tumors via oral ingestion. Additionally, food of any sort is not generally viewed to be able to kill cancer cells in vitro or in vivo.

It is therefore an aim of the present invention to provide and alternative composition and IV administration route for treating malignant neoplasms.

Effects of OPRGE on Type 2 Diabetes

Currently, garlic is becoming one of the most extensively studied herb drugs, and the positive effects of garlic supplements on blood glucose control and liquid regulation were further reported, which attracted more and more attention from researchers. A series of randomized controlled trials (RCTs) of high quality were designed to investigate its efficacy in the management of T2DM during last the decades. As a promising traditional food and medicine, together with its potential advantages of multiple targets, wide distribution, and rare complications, garlic would have a very important and significant influence on current clinical management of T2DM if its efficacy were confirmed. However, due to the limited sample size and verified outcomes, there is not yet a comprehensive and quantitative analysis with high reliability to demonstrate efficacy of oral garlic product as food or as medicine.

Studies confirm that additional garlic contributes to improved blood glucose control in 1-2 weeks as well as in 24 weeks in T2DM and plays positive roles in total cholesterol and high/low density lipoprotein regulation in 12 weeks. The potential sustained effects involving insulin resistance relief seems promising, however further studies are warranted to support the finding. ncbi.nlm.nih.gov/pmc/articles/PMC5642189/

It is therefore an aim of the present invention to provide and alternative composition and IV administration route fix treating type II diabetes.

Effects of OPRGE on Infectious Diseases

Garlic stimulates the immune system and acts as a natural antibiotic, not harmful to the friendly bacteria flora. Many laboratory studies have confirmed the antibacterial, antifungal, antivirus, immune-stimulating, and antioxidant properties of garlic.

Allicin, one of the active principles of freshly crushed garlic homogenates, has a variety of antimicrobial activities. Allicin in its pure form was found to exhibit i) antibacterial activity against a wide range of Gram-negative and Gram-positive bacteria, including multidrug-resistant enterotoxigenic strains of *Escherichia coli*; ii) antifungal activity, particularly against *Candida albicans*; iii) antiparasitic activity, including some major human intestinal protozoan parasites such as *Entamoeba histolytica* and *Giardia lamblia*; and iv) antiviral activity. bashaar.org.iVfiles/6130.pdf One study showed the both clinical and standard isolates of *S. aureus* and *E. coli* were highly sensitive to concentrations of 0.75 ml/20 ml of agar media in using diffusion method and Cork borers. Moreover, unlike clinical isolates of *S. aureus*, clinical isolate of *E. coli* was a bit resistant/not sensitive/at concentration of 0.5 ml/28 ml of media. This could be in regard with the nature permeability of *E. coli*, which means 20% of membrane of *E. coli* is made of lipid while that of *S. aureus* is only made of 2% lipid [2]. Therefore, the garlic extract was more important for the prevention of resistant *S. aureus* which is currently becoming a challenge developing resistance to many commercially available drugs like penicillin. infectious-diseases-and-treatment.imedpub.com/antibacterial-effect-of-garlic-allium-sativumagainst-clinical-isolates-of-staphylococcusaureus-and-escherichia-coli-from-patientsa.php?aid=17777

One observed that, as the concentration of the garlic extract increases, efficiency increased and hence inhibition and growth of test bacteria been diminished. As observed from the above tables, Larger clear zones at higher concentrations and lower clear zones at lower concentrations. This implies that, Garlic has both bacteriostatic and bactericidal effect.

Another study result indicated that, invitro, garlic extracts have inhibition properties against *C. albicans* and MRSA but weak inhibition properties against *P. aeruginosa*, while it had the potential to improve the effect of antibiotics on antibiotic resistant pathogens. ncbi.nlm.nih.gov/pmc/articles/PMC4458355/

It is therefore an aim of the present invention to provide and alternative composition and IV administration route for treating infectious diseases.

The invention claimed is:

1. A pharmaceutical composition comprising an organic phase of raw garlic extract (OPRGE) prepared by the following steps: (a) blending raw garlic cloves in sterile water ($H_2O$) to produce a garlic juice; (b) filtering the garlic juice to remove particles and to obtain a water extraction of raw garlic (WERG) solution; (c) adding an equal volume of a chloroform/methanol (1:1 v/v) solvent to the WERG; (d) after thorough homogenization, adding an equal volume of 1-butanol/50 mM NaCl (4:5, v/v), followed by vortexing and sonicating till being completely mixed to obtain a mixture; (e) centrifuging the mixture for no less than 10 min at a temperature of 45° F. to 75° F. to obtain three phases: a colorless upper aqueous phase, a white solid interphase, and a light yellowish lower organic phase; and (f) collecting the organic phase carefully, followed by drying under a flow of nitrogen gas to obtain the OPRGE.

2. The pharmaceutical composition according to claim 1, wherein the garlic is *Allium sativum*.

3. The pharmaceutical composition according to claim 1, wherein the pharmaceutical composition is formulated for an intravenous (IV), intraperitoneal (IP), or topical application.

4. The pharmaceutical composition according to claim 1, wherein the OPRGE is dissolved in 99.9% (w/v) DMSO (dimethyl sulfoxide) to prepare an intravenous infusion formulation.

5. The pharmaceutical composition according to claim 4, wherein the dissolved OPRGE is added to a pharmaceutically acceptable carrier selected from a 0.45% or 0.9% (w/v) Normal Saline, Lactated Ringers, or 5% (w/v) Dextrose to prepare an intravenous infusion formulation containing up to 5% (w/v) of DMSO and 5% (w/v) of OPRGE.

* * * * *